US00PP27544P3

(12) United States Plant Patent
Jelenkovic et al.

(10) Patent No.: US PP27,544 P3
(45) Date of Patent: Jan. 17, 2017

(54) STRAWBERRY PLANT NAMED 'NJ08-08-6'

(50) Latin Name: *Fragaria ananassa*
Varietal Denomination: NJ08-08-6

(71) Applicant: Rutgers, The State University, New Brunswick, NJ (US)

(72) Inventors: Gojko J. Jelenkovic, Piscataway, NJ (US); Peter J. Nitzsche, Long Valley, NJ (US); William T. Hlubik, Bordentown, NJ (US); Jessica D. Baculis, Watchung, NJ (US)

(73) Assignee: Rutgers, The State University, New Brunswick, NJ (US)

( * ) Notice: Subject to any disclaimer, the term of this patent is extended or adjusted under 35 U.S.C. 154(b) by 5 days.

(21) Appl. No.: 13/999,929

(22) Filed: Apr. 4, 2014

(65) Prior Publication Data

US 2015/0289430 P1 Oct. 8, 2015

(51) Int. Cl.
*A01H 5/08* (2006.01)

(52) U.S. Cl.
USPC ..... Plt./208

(58) Field of Classification Search
USPC ..... Plt./208, 209
See application file for complete search history.

*Primary Examiner* — Susan McCormick Ewoldt
(74) *Attorney, Agent, or Firm* — James A. Lucas; Driggs, Hogg, Daugherty & Del Zoppo Co., LPA

(57) ABSTRACT

A new and distinct cultivar of strawberry plant (*Fragaria*× *ananassa*), was developed from seed produced by a hand pollinated cross between 'NJ01-73-3' and 'NJ03-232-2'. The new strawberry plant named 'NJ08-08-6' is distinguished by its highly vigorous, upright growth habit, high productivity, uniform fruit color and shape, and excellent fruit quality and flavor.

2 Drawing Sheets

Latin name of genus and species of the plant claimed: *Fragaria ananassa.*
Variety denomination: 'NJ08-08-6'.

CROSS REFERENCE TO RELATED APPLICATIONS

NONE

STATEMENT REGARDING FEDERALLY SPONSORED RESEARCH OR DEVELOPMENT

NONE

BACKGROUND OF THE NEW PLANT

A new and distinct cultivar of strawberry named 'NJ08-08-6' is a short day cultivar similar to 'Chandler' (U.S. Plant Pat. No. 5,262). The new cultivar is distinguished by its upright petioles and large, shiny fruit with a uniform red color, uniform conical shape and excellent flavor. The cultivar is well adapted to high density plasticulture growing systems and has been shown to perform well in the eastern United States. This new variety should be of commercial value, particularly for farmers that sell fruit for fresh consumption directly to consumers in pick-your- own operations and at farmers markets.

ORIGIN OF THE VARIETY

The new 'NJ08-08-6' strawberry genotype was developed from a controlled cross of 'NJ01-73-3' (unpatented) as the female parent and 'NJ03-232-2' (unpatented) as the male parent. The female parent 'NJ01-73-3' was chosen for its vigorous growth habit, high productivity, large fruit and excellent fruit firmness; however, its fruit is poorly colored and lacks flavor. The male parent 'NJ03-232-2' was chosen for the excellent flavor of its fruit. Both parental genotypes are derivatives of many cycles of crosses and selection in a controlled breeding program at a major New Jersey university. Seeds of the cross were germinated in a greenhouse and planted in the field at a research farm in New Brunswick, N.J. in 2008. After the first round of selection, the plant was evaluated for two seasons in small observational plots. The selected plant designated as 'NJ08-08-6', was recognized as the best combination of parental phenotypes, including high vigor, high productivity, and large flavorful fruit of uniform shape and color. The 'NJ08-08-6' plant was then asexually propagated using stolons for further evaluations from 2012 to 2016 in observational and replicated trials in several locations in New Jersey, one location in North Carolina and one location in Maryland.

SUMMARY OF THE VARIETY

The 'NJ08-08-6' plant is primarily adapted to the climate and conditions of the eastern United States (zones 5b, 6a & b, 7a & b, and 8a & b) where it demonstrates vigorous, upright plant growth, resulting in observational reductions in strawberry pathogens. It is characterized by its high production of large, uniformly ripened and uniformly conically shaped fruit, with exceptionally sweet and aromatic flavors.

BRIEF DESCRIPTION OF THE PHOTOGRAPHS

DETAILED BOTANICAL DESCRIPTION

Color references below are measured against The Royal Horticultural Society Colour Chart (R.H.S. 5$^{th}$ Ed. 2007). Colors of foliage, flowers and fruit may vary with the age of the plant part, and variations in abiotic conditions.

Figure 2:
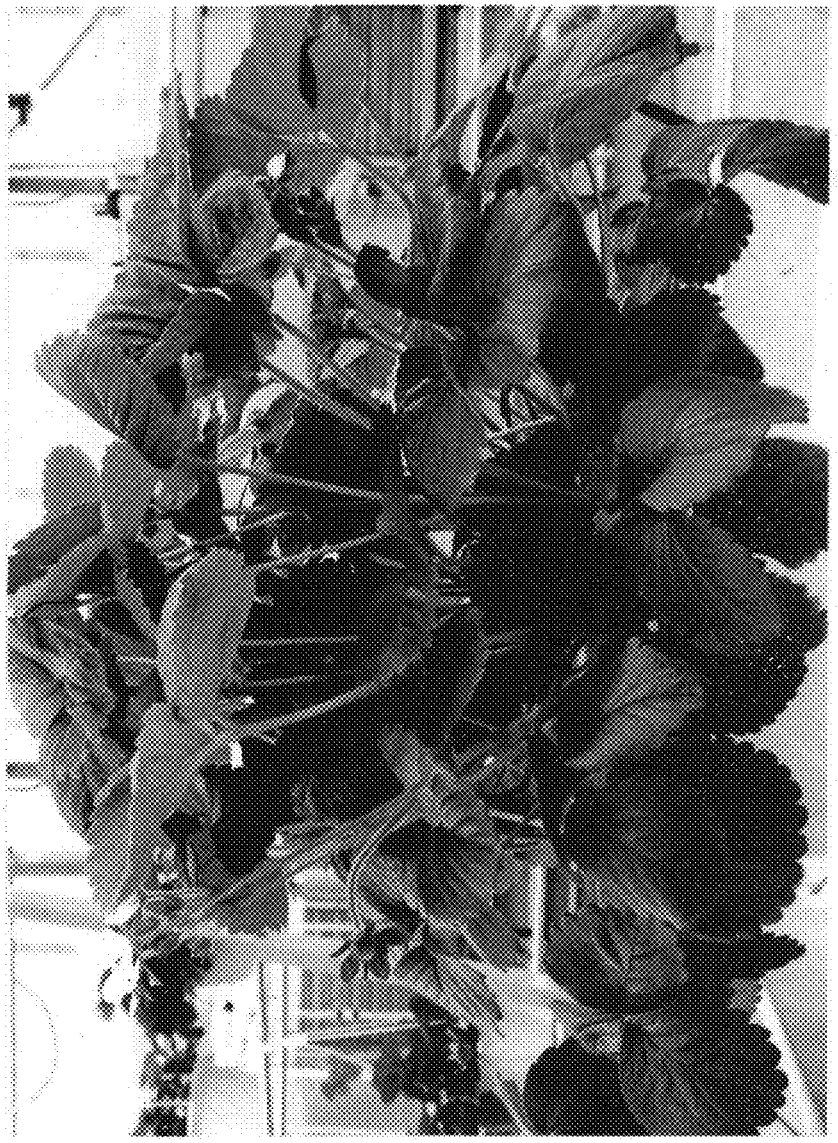
FIG. 2 illustrates the characteristic upright growth pattern of the mature petioles and foliage of 'NJ08-08-6'.

The 'NJ08-08-6' plant can be distinguished from other strawberry varieties by the structure of its foliar growth. In the spring as the leaves arise from the crowns there is a rapid elongation of the petioles causing an elevation of the leaf lobes and an upright mode of growth (FIG. 2). The petioles are very sturdy and remain in an upright position for most of the growing season.

Strawberry plant diameter and height are affected by the production system and abiotic and biotic conditions during overwintering and the following growing season. In the plasticulture system used in Pittstown, N.J., with plants grown 30 cm apart in double staggered rows, average 'NJ08-08-6' plant diameter (not including stolons) was 38 cm and average plant height was 28 cm. Measurements at the end of the harvest showed that 'NJ08-08-6' had developed 5 crowns per plant and 4 stolons per crown on average (Pittstown, N.J. 2016).

'NJ08-08-6' leaves have 3 leaflets. Leaf width, measured with the 3 leaflets flattened, averages 18 cm. Leaf petiole length is 11 to 32 cm, leaf petiole diameter is 0.4 cm. Leaf petioles are green (RHS 146D) and have upwards and outwards hair. Stipules at the base of the petiole are 3.2 cm long and 0.7 cm wide on average. The stipule surface is smooth and light green with medium anthocyanin coloration (RHS N34C).

The terminal leaflet has an obtuse shape of base, and serrate to crenate margin with 23 serrations on average. The terminal leaflet blade is 9.6 cm long and 8.3 cm wide on average. The upper leaflet surface color is green (RHS 137A-B) and the lower leaflet surface color is yellow-green (RHS 148A). Terminal leaflet petiolule length averages 1.3 cm, and petiolule diameter averages 0.2 cm. The petiolule color is green (RHS 146D).

The position of the 'NJ08-08-6' inflorescence is level with the foliage. 'NJ08-08-6' plants are in full flower early to mid-May (Pittstown, N.J., 2016). 'NJ08-08-6' plants developed 35 to 62 flowers per plant with an average of 46 flowers per plant (Pittstown, N.J., 2016). 'NJ08-08-6' flowers have 5 petals and 10 sepals on average. 'NJ08-08-6' flower petals are white (RHS 155B), have a smooth edge, and are usually not touching. 'NJ08-08-6' petals are as long as wide (Table 1), and have a rounded shape on the outside of the flower, but a convergent shape at the base of the flower. 'NJ08-08-6' petal characteristics differ from those of 'Chandler' which has overlapping petals that are slightly shorter than wide with a round shape both on the outside and the base of the flower (except for a small rectangular petal attachment to the base). The 'NJ08-08-6' flower pedicel has hair with a horizontal attitude (as opposed to upwards for 'Chandler'). Flowers have numerous pistils and usually 24 to 30 anthers.

'NJ08-08-6' fruit trusses are 19 cm long on average. 'Chandler' fruit trusses are usually longer with an average of 25 cm. In plasticulture, fruit trusses often lay on the plastic around the crowns because of the weight of the fruit.

The upright foliage and prostate fruit trusses make the lower parts of the 'NJ08-08-6' bush more open to air movement and the micro-environment less favorable for the development of leaf and fruit diseases. During the two year observational field evaluations at a research farm in New Brunswick, N.J., no pesticides or other protective measures were used. During this time, the plant displayed no visually detrimental symptoms of disease on its foliage or fruit.

The time from flowering to fruit ripening (harvest) ranges from 28-34 days, which categorizes this genotype as a mid-season variety. Fruit turns red acropetally, from the fruit calyx toward the tip. Under particularly warm conditions in the spring, a primary fruit can become completely red in a single day; however, formation of sugars, aromatics and other quality constituents requires at least 2 additional days.

Figure 1:
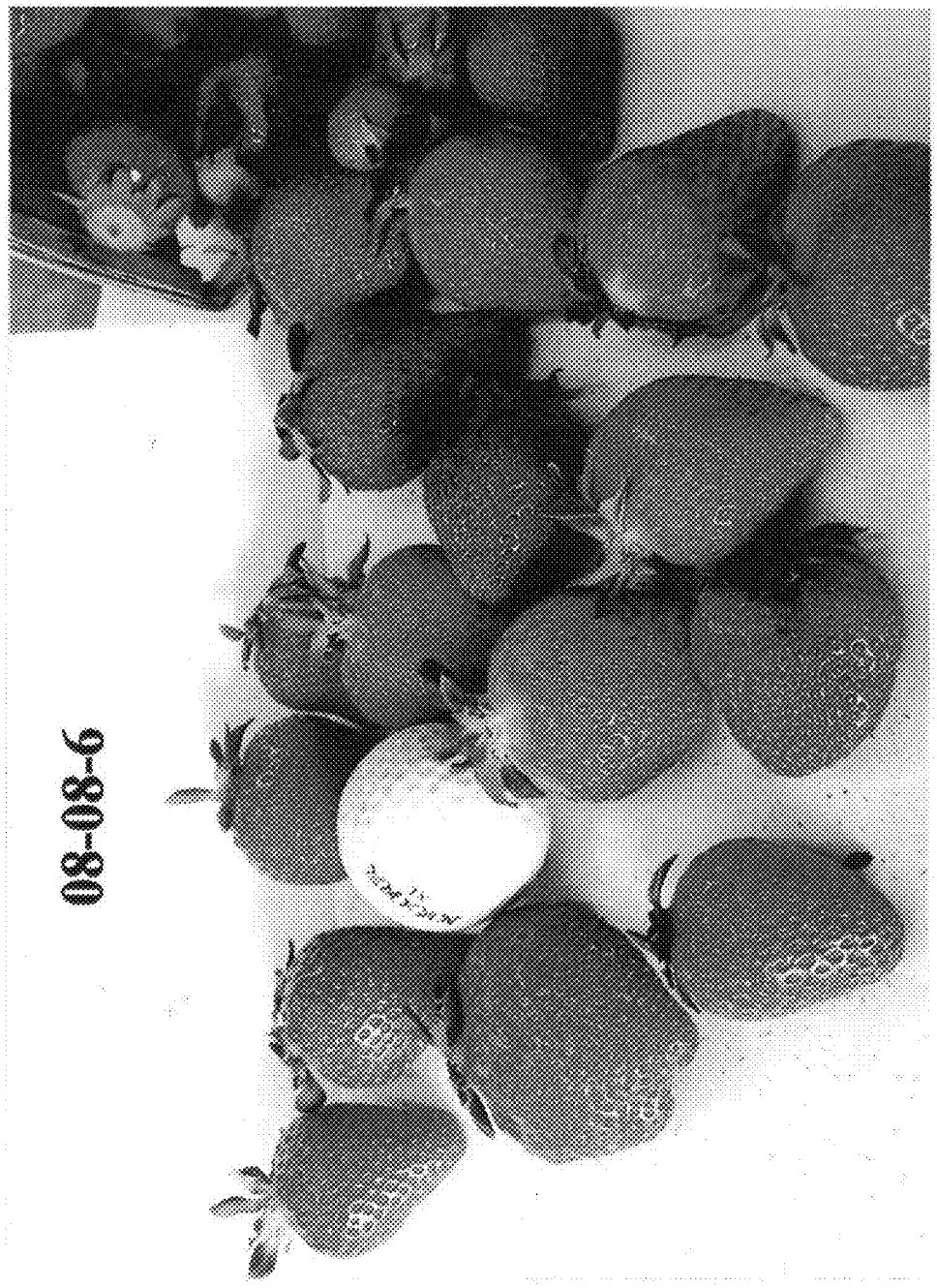
FIG. 1 illustrates the characteristics (shape, size and coloring) of typical ripened 'NJ08-08-6' fruit.

The most distinctive feature of the 'NJ08-08-6' plant is the ripened fruit (FIG. 1). 'NJ08-08-6' fruit has an appealing shiny red color (RHS 44C and RHS 45C), and a uniform conical shape with a length/width ratio of 1.3 for both primary and secondary fruit (TABLE 2). Fruit flesh and core are red (flesh RHS 46B, core RHS 44B). Achenes are yellow-green (RHS 152D-153C). The position of the achenes is level with the fruit surface. The number of achenes counted on 5 secondary fruit averaged 190. 'NJ08-08-6' weighted average fruit weight was large in most trials, but varied in magnitude relative to 'Chandler' (TABLE 3).

'NJ08-08-6' fruit is smooth, solid and firm when handled and displays some degree of resistance to fruit rot. The sweetness and aroma of the fruit supersedes the quality found in known commercially grown strawberry varieties. During the 2013 season strawberries from the 'NJ08-08-6' plants were compared with 'Chandler' by 20 panelists at one of the research locations. In this survey 'NJ08-08-6' rated higher for sweetness, acidity and overall flavor compared to 'Chandler'. This is confirmed by data of percentage Brix which is usually higher for 'NJ08-08-6' than for 'Chandler' fruit (TABLE 3).

TABLE 1

Flower characteristics of 'NJ08-08-6' and 'Chandler', Pittstown, New Jersey 2016

| Characteristic[x] | 'NJ08-08-6' | 'Chandler' |
|---|---|---|
| Corolla diameter (mm) | 33 | 33 |
| Calyx diameter (mm) | 25 | 27 |
| Petal length (mm) | 14 | 13 |
| Petal width (mm) | 14 | 15 |
| Petal color | White (155B) | White (155B) |
| Inner Sepal length (mm) | 9 | 10 |
| Outer Sepal length (mm) | 9 | 7 |
| Inner Sepal width (mm) | 6 | 5 |
| Outer Sepal width (mm) | 5 | 5 |
| Sepal color | Green (141A) | Green (141A) |

[x]Data are averages of 10 observations on secondary flowers. Petals and sepals were spread out flat for corolla and calyx diameter measurements. Color references are measured against The Royal Horticultural Society Colour Chart (R.H.S. 5$^{th}$ Ed. 2007).

TABLE 2

Fruit characteristics of 'NJ08-08-6' and 'Chandler', Pittstown, New Jersey 2016

| Characteristic[x] | 'NJ08-08-6' | 'Chandler' |
|---|---|---|
| Primary Fruit Length (mm) | 47 | 40 |
| Primary Fruit Width (mm) | 36 | 35 |
| Primary Fruit Thickness (mm) | 32 | 32 |
| Primary Fruit Length/Width | 1.3 | 1.2 |
| Primary Fruit Weight (g) | 22 | 20 |
| Secondary Fruit Length (mm) | 42 | 36 |

TABLE 2-continued

| Fruit characteristics of 'NJ08-08-6' and 'Chandler', Pittstown, New Jersey 2016 | | |
|---|---|---|
| Characteristic[x] | 'NJ08-08-6' | 'Chandler' |
| Secondary Fruit Width (mm) | 32 | 34 |
| Secondary Fruit Thickness (mm) | 30 | 31 |
| Secondary Fruit Length/Width | 1.3 | 1.1 |
| Secondary Fruit Weight (g) | 17 | 17 |

[x]Data are averages of 20 measurements.

TABLE 3

| Field performance of 'NJ08-08-6' and 'Chandler' in New Jersey trials | | | |
|---|---|---|---|
| Trial Location and Harvest Year | 'NJ08-08-6' Marketable Yield[x] (lb/A) | 'NJ08-08-6' Weighted Average Fruit Weight[x,xx] (g) | 'NJ08-08-6' Brix[xxx] (%) |
| Pittstown 2013 | 13,520 | 19.9 | 7.5 |
| Pittstown 2014 | 8,093 | 16.8 | 8.8 |
| Pittstown 2015 | 15,205 | 15.1 | 7.5 |
| Pittstown 2016 | 12,992 | 16.5 | 9.6 |
| North Brunswick 2013 | 10,835 | 10.3 | 8.2 |
| North Brunswick 2014 | 11,120 | 17.0 | 9.3 |
| North Brunswick 2015 | 13,190 | 15.8 | 9.4 |

TABLE 3-continued

| Field performance of 'NJ08-08-6' and 'Chandler' in New Jersey trials | | | |
|---|---|---|---|
| Trial Location and Harvest Year | 'Chandler' Marketable Yield[x] (lb/A) | 'Chandler' Weighted Average Fruit Weight[x,xx] (g) | 'Chandler' Brix[xxx] (%) |
| Pittstown 2013 | 12,420 | 18.5 | 7.1 |
| Pittstown 2014 | 9,018 | 19.2 | 7.9 |
| Pittstown 2015 | 16,938 | 15.1 | 7.0 |
| Pittstown 2016 | 16,456 | 17.6 | 8.5 |
| North Brunswick 2013 | 4,191 | 12.0 | 8.3 |
| North Brunswick 2014 | 12,187 | 17.1 | 8.3 |
| North Brunswick 2015 | 16,193 | 17.9 | 7.7 |

[x]Data are averages of 4 plots, except for Pittstown 2013 'Chandler' (3 plots).

[xx]Weighted average fruit weight is total marketable yield divided by total number of fruit harvested per plot. Total number of fruit harvested per plot was estimated by dividing marketable yield by average fruit weight (determined on a sample of 20 fruit, or on all fruit if fewer than 20 present) for each harvest, and summing the number of fruit for all harvests.

[xxx]Brix was determined at part of the harvests. Brix data are averages of 4 harvests, except for Pittstown 2013 (2 harvests), and North Brunswick 2014 and 2015 (5 harvests).

We claim:

1. A new and distinct variety of strawberry plant, designated 'NJ08-08-6' substantially as herein shown and described.

* * * * *